United States Patent [19]

Johnson

[11] 4,237,059

[45] Dec. 2, 1980

[54] 2-DECARBOXY-2-HYDROXYMETHYL-TRANS-2,3,4,5-TETRADEHYDRO-9-DEOXY-5,9α-EPOXY-PGF$_1$ COMPOUNDS

[75] Inventor: Roy A. Johnson, Kalamazoo, Mich.

[73] Assignee: The Upjohn Company, Kalamazoo, Mich.

[21] Appl. No.: 73,461

[22] Filed: Sep. 7, 1979

Related U.S. Application Data

[60] Division of Ser. No. 936,295, Aug. 23, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.$^3$ .............................................. C07D 311/02
[52] U.S. Cl. .................................. 260/345.2; 542/426; 542/429
[58] Field of Search ...................... 260/345.2; 542/426, 542/429

[56] References Cited

PUBLICATIONS

Pace–Asciak et al., Biochem., 10, 3657 (1971).
Pace–Asciak et al., Jacs, 98, 2348 (1976).

*Primary Examiner*—Nicky Chan
*Attorney, Agent, or Firm*—Robert A. Armitage

[57] ABSTRACT

The present invention relates to novel 2-decarboxy-2-hydroxymethyl-trans-2,3,4,5-tetradehydro-9-deoxy-5,9α-epoxy-PGF$_1$ compounds, which are useful for inducing a variety of prostacyclin-like pharmacological effects. Accordingly, these compounds are useful pharmacological agents for the same purposes for which prostacyclin is employed.

8 Claims, No Drawings

2-DECARBOXY-2-HYDROXYMETHYL-TRANS-2,3,4,5-TETRADEHYDRO-9-DEOXY-5,9α-EPOXY-PGF₁ COMPOUNDS

DESCRIPTION

CROSS REFERENCE TO RELATED APPLICATION

The present application is a divisional application of U.S. Ser. No. 936,295, filed Aug. 23, 1978, now pending issuance as a United States patent; which is a divisional application of U.S. Ser. No. 819,856, filed July 28, 1977, now U.S. Pat. No. 4,123,441; which is a continuation-in-part application of U.S. Ser. No. 725,546, filed Sept. 22, 1976, now abandoned; which is a continuation-in-part application of U.S. Ser. No. 716,960, filed Aug. 23, 1976, now abandoned.

BACKGROUND OF THE INVENTION

The present invention relates to novel 2-decarboxy2-hydroxymethyl-trans-2,3,4,5-tetradehydro-9-deoxy-5,9α-epoxy-PGF₁ compounds, which are useful for inducing a variety of prostacyclin-like pharmacological effects. Accordingly, these compounds are useful pharmacological agents for the same purposes for which prostacyclin is employed.

The essential material constituting a disclosure of the preparation and use of the novel compounds of the present invention is incorporated here by reference from U.S. Pat. No. 4,123,441.

SUMMARY OF THE INVENTION

The present invention particularly provides:
a 4Z compound of the formula

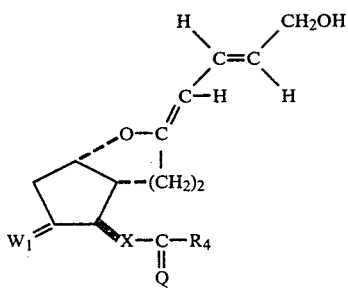

wherein $W_1$ is α-OH:β-H, α-H:β-OH, oxo, methylene, α-H:β-H, α-CH₂OH:β-H;

wherein Q is oxo, α-H:β-H, α-OH:β-R₈ or α-R₈:β-OH wherein $R_8$ is hydrogen or alkyl of one to 4 carbon atoms, inclusive; and wherein $R_4$ is
(1) —CR₅R₆—C$_g$H$_{2g}$-CH₃
(2) —CR₅R₆-Z-(Ph)
(3) cis-CH₂-CH=CH-CH₂CH₃ wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR₅R₆— and the (Ph); wherein (Ph) is phenyl or phenyl substituted by (T)s, wherein T is alkyl of one to 4 carbon atoms, inclusive, fluoro, chloro, trifluoromethyl, or —OR₇, wherein R₇ is alkyl of one to 4 carbon atoms, inclusive, and s is zero, one, 2, or 3, with the proviso that not more than two T's are other than alkyl and when s is 2 or 3 the T's are either the same or different; and wherein X is
(1) trans-CH=CH—,
(2) cis—CH=CH—,
(3) —C≡C—, or
(4) —CH₂CH₂—;

including the lower alkanoates thereof; and
a 4E compound of the formula

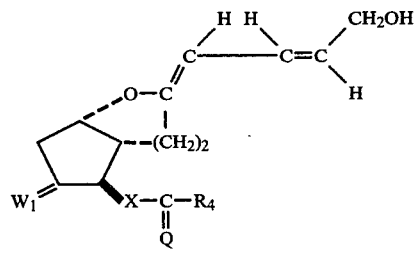

wherein $W_1$ is α-OH:β-H, α-H:β-OH, oxo, methylene, α-H:β-H, α-CH₂OH:β-H;

wherein Q is oxo, α-H-β-H, α-OH:β-R₈ or α-R₈:β-OH wherein $R_8$ is hydrogen or alkyl of one to 4 carbon atoms, inclusive; and wherein $R_4$ is
(1) —CR₅R₆—C$_g$H$_{2g}$—CH₃
(2) —CR₅R₆-Z-(Ph)
(3) cis-CH₂-CH=CH—CH₂CH₃ wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR₅R₆— and the (Ph); wherein (Ph) is phenyl or phenyl substituted by (T)s, wherein T is alkyl of one to 4 carbon atoms, inclusive, fluoro, chloro, trifluoromethyl, or —OR₇, wherein R₇ is alkyl of one to 4 carbon atoms, inclusive, and s is zero, one, 2, or 3, with the proviso that not more than two T's are other than alkyl and when s is 2 or 3 the T's are either the same or different; and wherein X is
(1) trans-CH=CH—,
(2) cis-CH=CH—,
(3) —C≡C—, or
(4) —CH₂CH₂—;

including the lower alkanoates thereof.

With regard to the divalent substituents described in the claims, e.g., Q and W₁, these divalent radicals are defined as α-R$_i$:β-R$_j$, where R$_i$ represents a substituent of the divalent moiety of the alpha configuration with respect to the cyclopentane and R$_j$ represents a substituent of the divalent moiety of the beta configuration with respect to the cyclopentane ring. Accordingly, when Q is defined as α-OH:β-$R_8$, the hydroxy of the Q moiety is in the alpha configuration, i.e., as in prostacyclin, and the $R_8$ substituent is in the beta configuration. Not all carbon atoms to which such divalent moieties are attached represent asymmetric centers. For example, when both valence bonds are to hydrogen (e.g., $W_1$ or Q is α-H:β-H), then no asymmetric center is present.

DESCRIPTION OF THE PREFERRED EMBODIMENTS

The present invention particularly relates to the following chemical compounds:

2-Decarboxy-2-hydroxymethyl-(4Z)-9-deoxy-5,9α-epoxy-$\Delta^4$-trans-$\Delta^2$-$PGF_1$;

2-Decarboxy-2-hydroxymethyl-(4Z)-9-deoxy-5,9α-epoxy-$\Delta^4$-trans-$\Delta^2$-(15S)-15-methyl-$PGF_1$;

2-Decarboxy-2-hydroxymethyl-(4Z)-9-deoxy-5,9α-epoxy-$\Delta^4$-trans-$\Delta^2$-16,16-dimethyl-$PGF_1$;

2-Decarboxy-2-hydroxymethyl-(4Z)-9-deoxy-5,9α-epoxy-$\Delta^4$-trans-$\Delta^2$-13,14-dihydro-$PGF_1$;

2-Decarboxy-2-hydroxymethyl-(4Z)-9-deoxy-5,9α-epoxy-$\Delta^4$-trans-$\Delta^2$-17-phenyl-18,19,20-trinor-$PGF_1$;

2-Decarboxy-2-hydroxymethyl-(4Z)-9-deoxy-5,9α-epoxy-$\Delta^4$-trans-$\Delta^2$-16-phenoxy-17,18,19,20-tetranor-$PGF_1$;

2-Decarboxy-2-hydroxymethyl-(4Z)-9-deoxy-5,9α-epoxy-$\Delta^4$-trans-$\Delta^2$-16-(m-chlorophenoxy)-17,18,19,20-tetranor-$PGF_1$;

2-Decarboxy-2-hydroxymethyl-(4Z)-9-deoxy-5,9α-epoxy-$\Delta^4$-trans-$\Delta^2$-16-(α,α,α-trifluoro-p-tolyloxy)-17,18,19,20-tetranor-$PGF_1$;

2-Decarboxy-2-hydroxymethyl-(4Z)-9-deoxy-5,9α-epoxy-$\Delta^4$-trans-$\Delta^2$-13,14-dihydro-16-phenoxy-17,18,19,20-tetranor-$PGF_1$; and 2-Decarboxy-2-hydroxymethyl-(4E)-9-deoxy-5,9α-epoxy-$\Delta^4$-trans-$\Delta^2$-$PGF_1$.

I claim:
1. A 4Z compound of the formula

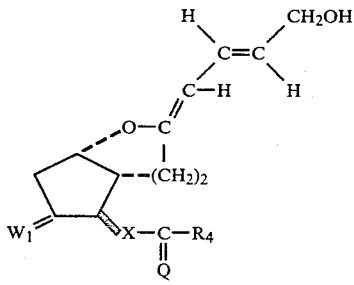

wherein $W_1$ is α-OH:β-H, α-H:β-OH, oxo, methylene, α-H:β-H, α-$CH_2OH$:β-H;

wherein Q is oxo, α-H:β-H, α-OH:β-$R_8$ or α-$R_8$:β-OH wherein $R_8$ is hydrogen or alkyl of one to 4 carbon atoms, inclusive; and wherein $R_4$ is
 (1) —$CR_5R_6$—$C_gH_{2g}$—$CH_3$
 (2) —$CR_5R_6$—Z-(Ph)
 (3) cis—$CH_2$—CH=CH—$CH_2CH_3$ wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the (Ph); wherein (Ph) is phenyl or phenyl substituted by (T)s, wherein T is alkyl of one to 4 carbon atoms, inclusive, fluoro, chloro, trifluoromethyl, or —$OR_7$, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is
 (1) trans—CH=CH—,
 (2) cis—CH=CH—,
 (3) —C≡C—, or
 (4) —$CH_2CH_2$—;

including the lower alkanoates thereof.

2. A compound according to claim 1, wherein Q is α-OH:β-$R_8$ or α-$R_8$:β-OH, and $W_1$ is α-OH:β-H, α-H:β-OH, or β-H:β-H.

3. A compound according to claim 2, wherein $W_1$ is α-OH:β-H.

4. A compound according to claim 3, wherein Q is α-OH:β-$R_8$.

5. A compound according to claim 4, wherein $R_4$ is —$CR_5R_6$—$C_gH_{2g}$—$CH_3$.

6. A compound according to claim 4, wherein $R_4$ is —$CR_5R_6$(Ph).

7. A 4E compound of the formula

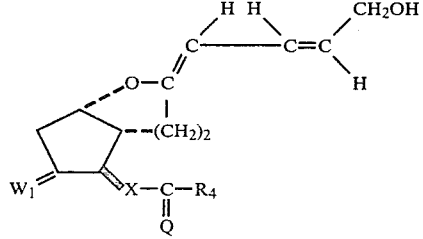

wherein $W_1$ is α-OH:β-H, α-H:β-OH, oxo, methylene, α-H:β-H, α-$CH_2OH$:β-H;

wherein Q is oxo, α-H:β-H, α-OH:β-$R_8$ or α-$R_8$:β-OH wherein $R_8$ is hydrogen or alkyl of one to 4 carbon atoms, inclusive; and wherein $R_4$ is
 (1) —$CR_5R_6$—$C_gH_{2g}CH_3$
 (2) —$CR_5R_6$—Z-(Ph)

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the (Ph); wherein (Ph) is phenyl or phenyl substituted by (T)s, wherein T is alkyl of one to 4 carbon atoms, inclusive, fluoro, chloro, trifluoromethyl, or —$OR_7$, wherein $R_7$ is alkyl of one to 4 carbon atoms, inclusive, and s is zero, one, 2, or 3, with the proviso that not more than two T's are other than alkyl and when s is 2 or 3 the T's are either the same or different; and wherein X is
(1) trans-CH=CH—,
(2) cis—CH=CH—,
(3) —C≡C—, or
(4) —CH$_2$CH$_2$—;

including the lower alkanoates thereof.

8. A compound according to claim 7, wherein Q is α-OH:β-R$_8$, wherein W$_1$ is α-OH:β-H, and wherein R$_4$ is —CR$_5$R$_6$—C$_g$H$_{2g}$—CH$_3$.

UNITED STATES PATENT OFFICE
CERTIFICATE OF CORRECTION

Patent No. 4,237,059  Dated 2 December 1980

Inventor(s) Roy A. Johnson

It is certified that error appears in the above-identified patent and that said Letters Patent are hereby corrected as shown below:

Column 4, line 23, "$\beta$-H:$\beta$-H." should read -- $\alpha$-H:$\beta$-H. --; line 52, "-$CR_5R_6$-$C_gH_{2g}CH_3$" should read -- -$CR_5R_6$-$C_gH_{2g}$-$CH_3$ --; line 54 should read -- (3) cis-$CH_2$-CH=CH-$CH_2CH_3$ --.

Signed and Sealed this

Seventh Day of April 1981

[SEAL]

Attest:

RENE D. TEGTMEYER

Attesting Officer     Acting Commissioner of Patents and Trademarks